(12) United States Patent
Usui

(10) Patent No.: US 6,261,846 B1
(45) Date of Patent: *Jul. 17, 2001

(54) GENE AMPLIFYING METHOD

(75) Inventor: Mitsugu Usui, Abiko (JP)

(73) Assignee: Sanko Junyaku Co. Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/292,563

(22) Filed: Apr. 15, 1999

(30) Foreign Application Priority Data

Nov. 9, 1998 (JP) .................................................. 10-318056
Mar. 10, 1999 (JP) .................................................. 11-063476

(51) Int. Cl.[7] .......................... G01N 33/00; C07H 21/02; C07H 21/04; C12Q 1/68; C12P 19/34
(52) U.S. Cl. .......................... 436/94; 536/23.1; 536/24.3; 536/24.33; 435/6; 435/91.1
(58) Field of Search ............................. 435/6, 91.1, 91.2, 435/7.1; 536/23.1, 24.3, 24.33; 436/94

(56) References Cited

U.S. PATENT DOCUMENTS

| | | | |
|---|---|---|---|
| 5,175,270 | * 12/1992 | Nilsen et al. | 536/27 |
| 5,273,882 | * 12/1993 | Snitman et al. | 435/6 |
| 5,437,977 | * 8/1995 | Segev | 435/6 |
| 5,484,904 | * 1/1996 | Nilsen et al. | 536/23.1 |
| 5,487,973 | * 1/1996 | Nilsen et al. | 435/6 |
| 5,605,793 | * 2/1997 | Stemmer et al. | 435/6 |
| 5,834,252 | * 11/1998 | Stemmer et al. | 435/91.1 |

OTHER PUBLICATIONS

Prodromou et al., Recursive PCR: a novel technique for total gene synthesis. Protein Engineering, 5, 827–829, 1992.*

* cited by examiner

Primary Examiner—Ethan Whisenant
Assistant Examiner—Frank Lu
(74) Attorney, Agent, or Firm—Wenderoth, Lind & Ponack, L.L.P.

(57) ABSTRACT

A gene amplifying method for efficiently amplifying a gene without using enzyme or branched DNA. A plurality of pairs of probes each composed of three or more portions complementary to such portions in the other probe are used, and hybridized such that they cross in alternation to form a double-stranded polymer.

33 Claims, 16 Drawing Sheets

FIG.1

PROBE NO.1

5'—TgC Cgg ACC AgC gAg Cgg · TAg CAg gAT CCC TCT AAg · CTT ATT CAg TAT CgA gTA—3'
　　　　　X-REGION　　　　　　　　　　Y-REGION　　　　　　　　　Z-REGION

PROBE NO.2

3'—gAA TAA gTC ATA gCT CAT · ATC gTC CTA ggg AgA TTC · ACg gCC Tgg TCg CTC gCC—5'
　　　　　Z'-REGION　　　　　　　　　　Y'-REGION　　　　　　　　　X'-REGION

FIG.7

(PROBE NO.3)

5'— TgC CgA CC gg CgA gCg · TAg CAT gg CC CTC TAg · CTT ATC gg CC TCg AgA —3'

(PROBE NO.4)

3'— gAA TAg CC gg AgC TCT · ATC gTA CC gg gAg ATC · ACg gCT gg CC gCT CgC —5'

FIG.9

(PROBE NO.5)

5-TgA CTT ACT TAA CCg gTA AAA CAT · AAg CAg gAT CCT CTA AgC CTg A · CgA AgT ACA gTC Cgg Tgg Tg-3

X-REGION (24 BASES)　　Y-REGION (22 BASES)　　Z-REGION (20 BASES)

(PROBE NO.6)

3-gCT TCA TgT CAg gCC ACC AC · TTC gTC CTA ggA gAT TCg gAc T · ACT gAA TgA ATT ggC CAT TTT gTA-5

Z'-REGION (20 BASES)　　Y'-REGION (22 BASES)　　X'-REGION (24 BASES)

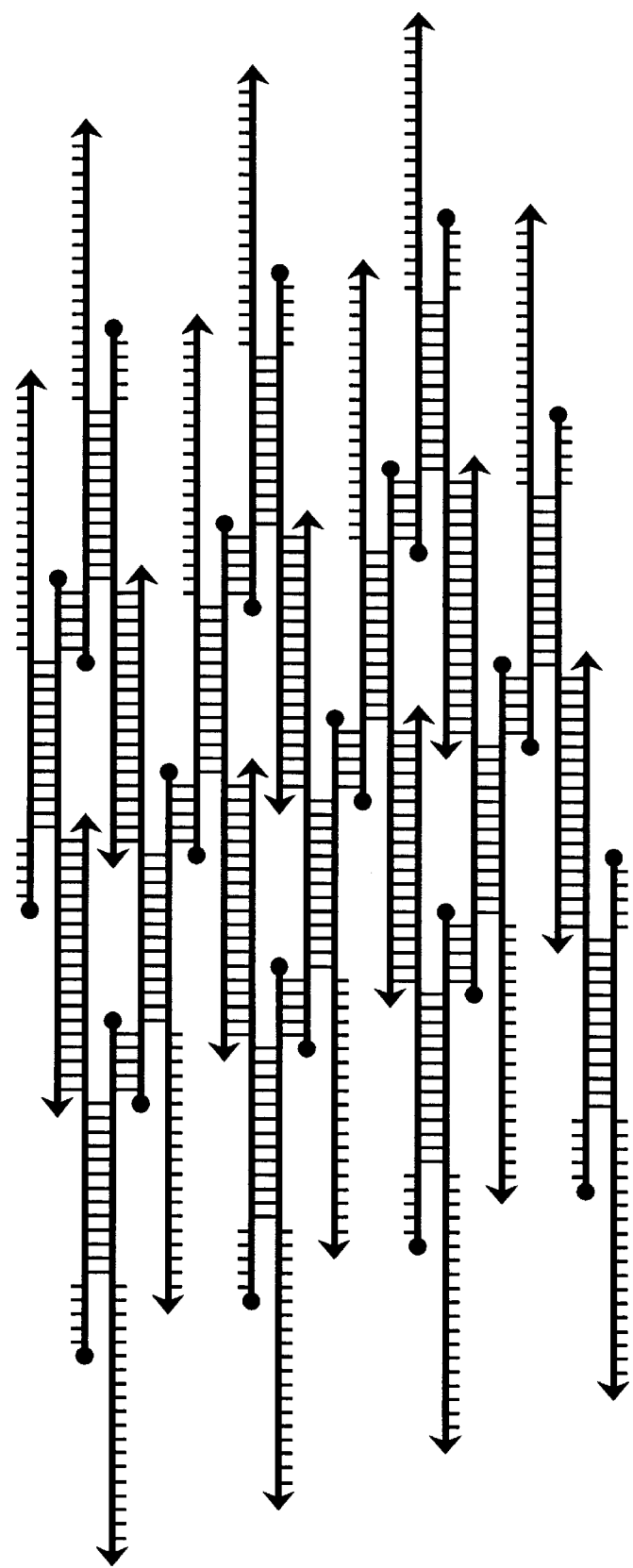
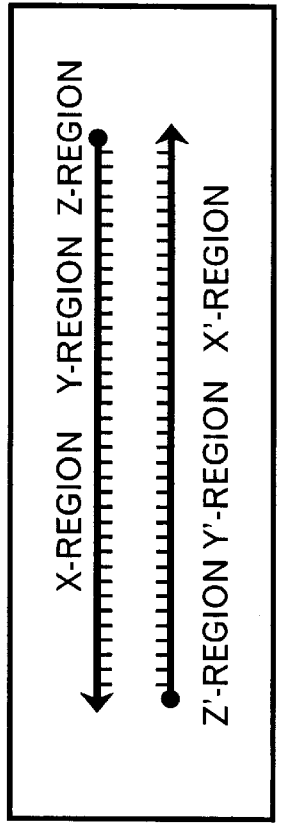
FIG.10

FIG. 14

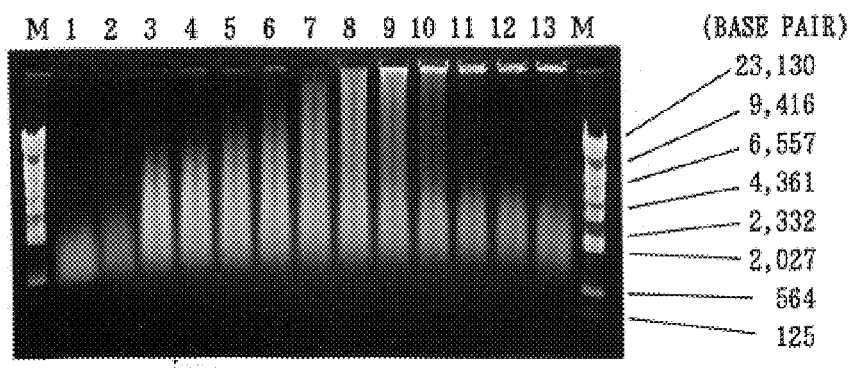

---

AGAROSE GEL CONCENTRATION: 0.5%
M: DNA SIZE MARKER (λ Hind III digest)
1: GENE AMPLIFYING PROBE 1 ONLY;
2: GENE AMPLIFYING PROBE 2 ONLY;
3: PAIR OF GENE AMPLIFYING PROBES AMPLIFIED AT HYBRIDIZATION TEMPERATURE OF 50°C;
4: PAIR OF GENE AMPLIFYING PROBES AMPLIFIED AT HYBRIDIZATION TEMPERATURE OF 52°C;
5: PAIR OF GENE AMPLIFYING PROBES AMPLIFIED AT HYBRIDIZATION TEMPERATURE OF 54°C;
6: PAIR OF GENE AMPLIFYING PROBES AMPLIFIED AT HYBRIDIZATION TEMPERATURE OF 56°C;
7: PAIR OF GENE AMPLIFYING PROBES AMPLIFIED AT HYBRIDIZATION TEMPERATURE OF 58°C;
8: PAIR OF GENE AMPLIFYING PROBES AMPLIFIED AT HYBRIDIZATION TEMPERATURE OF 60°C;
9: PAIR OF GENE AMPLIFYING PROBES AMPLIFIED AT HYBRIDIZATION TEMPERATURE OF 62°C;
10: PAIR OF GENE AMPLIFYING PROBES AMPLIFIED AT HYBRIDIZATION TEMPERATURE OF 64°C;
11: PAIR OF GENE AMPLIFYING PROBES AMPLIFIED AT HYBRIDIZATION TEMPERATURE OF 66°C;
12: PAIR OF GENE AMPLIFYING PROBES AMPLIFIED AT HYBRIDIZATION TEMPERATURE OF 68°C;
13: PAIR OF GENE AMPLIFYING PROBES AMPLIFIED AT HYBRIDIZATION TEMPERATURE OF 70°C;

AGAROSE GEL CONCENTRATION: 2.0%
M1: DNA SIZE MARKER (1Kb DNA Ladder)
M2: DNA SIZE MARKER (50b DNA Ladder)
1 : GENE AMPLIFYING PROBE 3 ONLY;
2 : GENE AMPLIFYING PROBE 4 ONLY;
3 : PAIR OF AMPLIFIED GENE AMPLIFYING PROBES; and
4 : PAIR OF AMPLIFIED GENE AMPLIFYING PROBES CLEAVED BY RESTRICTION ENZYME Hae III.

$10^{10} \sim 10^{1}$: HCV-RNA AMOUNT (NUMBER OF COPIES)

SEQUENCE LISTING

<160> NUMBER OF SEQ ID NOS: 16

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: synthetic

<400> SEQUENCE: 1
tgacttactt aaccggaaac ataagcagga tcctctaagc ctgacgaagt atttaacggt     60
ggtatg                                                               66

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: synthetic

<400> SEQUENCE: 2
atgtttccgg ttaagtaagt catcaggctt agaggatcct gcttcatacc accgttaaat     60
acttcg                                                               66

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: synthetic

```
<400> SEQUENCE: 3
tgccgaccgg cgagcgtagc atggccctct agcttatcgg cctcgaga                48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 4
cgctcgccgg tcggcactag agggccatgc tatctcgagg ccgataag                48

<210> SEQ ID NO 5
<211> LENGTH: 45
<212> TYPE: DNA
<213> ORGANISM: Artificial Sequence
<220> FEATURE:
<221> NAME/KEY: misc_feature
<222> LOCATION: (1)
<223> OTHER INFORMATION: phosphoric acid attached at 5' end
<220> FEATURE:
<223> OTHER INFORMATION: Description of Artificial Sequence: synthetic

<400> SEQUENCE: 5
tagagcgtgc agatagtcga tcctcacagg ggagtgattc atggt                   45

<210> SEQ ID NO 6
<211> LENGTH: 45
<212> TYPE: DNA
<213> ORGANISM: Artificial Sequence
<220> FEATURE:
<221> NAME/KEY: misc_feature
<222> LOCATION: (1)
<223> OTHER INFORMATION: biotin label attached at the 5' end
<220> FEATURE:
<223> OTHER INFORMATION: Description of Artificial Sequence: synthetic

<400> SEQUENCE: 6
tagagcgtgc agatagtcga tcctcacagg ggagtgattc atggt                   45

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 7
tactcgatac tgaataagcc tcacagggga gtgattcat                          39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 8
tactcgatac tgaataaggt tgatccaaga aaggacccg                          39

<210> SEQ ID NO 9
<211> LENGTH: 39
<212> TYPE: DNA
<213> ORGANISM: Artificial Sequence
<220> FEATURE:
```

-continued

<223> OTHER INFORMATION: Description of Artificial Sequence: synthetic

<400> SEQUENCE: 9
tactcgatac tgaataagcc tttcgcgacc caacactac                             39

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence: synthetic

<400> SEQUENCE: 10
cttattcagt atcgagtata gcaggatccc tctaagtgcc ggaccagcga gcgg           54

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: synthetic

<400> SEQUENCE: 11
tactcgatac tgaataagct tagagggatc ctgctaccgc tcgctggtcc ggca           54

<210> SEQ ID NO 12
<211> LENGTH: 54
<212> TYPE: DNA
<213> ORGANISM: Artificial Sequence
<220> FEATURE:
<221> NAME/KEY: misc_feature
<222> LOCATION: (1)
<223> OTHER INFORMATION: biotin label attached at the 3' end
<220> FEATURE:
<223> OTHER INFORMATION: Description of Artificial Sequence: synthetic

<400> SEQUENCE: 12
tactcgatac tgaataagct tagagggatc ctgctaccgc tcgctggtcc ggca           54

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: synthetic

<400> SEQUENCE: 13
tgccggacca gcgagcggta gcaggatccc tctaagctta ttcagtatcg agta           54

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: synthetic

<400> SEQUENCE: 14
ccgctcgctg gtccggcact tagagggatc ctgctatact cgatactgaa taag           54

<210> SEQ ID NO 15
<211> LENGTH: 66
<212> TYPE: DNA
<213> ORGANISM: Artificial Sequence
<220> FEATURE:
<223> OTHER INFORMATION: Description of Artificial Sequence: synthetic

<400> SEQUENCE: 15

-continued

```
tgacttactt aaccggtaaa acataagcag gatcctctaa gcctgacgaa gtacagtccg      60
gtggtg                                                                 66

<210> SEQ ID NO 16
<211> LENGTH: 66
<212> TYPE: DNA
<213> ORGANISM: Artificial Sequence
<220> FEATURE:
<223> OTHER INFORMATION: Description of Artificial Sequence: synthetic

<400> SEQUENCE: 16
atgttttacc ggttaagtaa gtcatcaggc ttagaggatc ctgcttcacc accggactgt      60
acttcg                                                                 66
```

GENE AMPLIFYING METHOD

BACKGROUND OF THE INVENTION

1. Field of the Invention

The present invention relates to special and novel probes, a gene amplifying method using cross (alternate) binding of the special probes, and a method of directly detecting a target gene and a method of detecting antigen/antibody using the gene amplifying method.

2. Description of the Related Art

In recent years, a method of amplifying a gene using a DNA polymerase, represented by a polymerase chain reaction method (hereinafter called the "PCR method"), a method of amplifying a gene by hybridizing polymer DNA having previously branched single-stranded DNA (hereinafter called the "branched DNA probe method"), and so on have been developed for detecting a very small amount of target gene.

The amplification of gene by the PCR method involves annealing hybridize) a primer complementary to a target gene (or a primer), and amplifying the gene through rise and fall of temperature using a thermostable DNA polymerase. Disadvantageously, this method takes a long time from amplification to detection of a gene, and is expensive. In addition, the amplification efficiency and specificity may vary depending on the design of a primer complementary to the target gene.

The amplification of gene by the branched DNA probe method, on the other hand, involves previously synthesizing a branched polymer single-stranded DNA probe, and hybridizing the branched polymer single-stranded DNA probe to a target gene to detect the target gene. However, the hybridization of the branched polymer single-stranded DNA probe to the target gene takes a long time because the branched DNA probe is a polymer. In addition, the branched polymer single-stranded DNA is limited in size, so that the detection of the target gene is also limited.

OBJECT AND SUMMARY OF THE INVENTION

The present invention has been made in view of the problems of the prior art mentioned above, and its object is to provide a method of efficiently amplify a gene without using enzyme or branched DNA.

To solve the problem mentioned above, a gene amplifying method according to the present invention comprises the steps of providing a plurality of pairs of probes each composed of three or more portions complementary to such portions of the other probe; and hybridizing said pairs of probes such that they cross in alternation to form a double-stranded polymer.

The pair of probes for use in the gene amplifying method, may be two DNA probes, a DNA probe and an RNA probe, two RNA probes, two PNA (Peptide Nucleic Acid or Polyamide Nucleic Acid) probes, a PNA probe and a DNA probe, or a PNA probe and an RNA probe.

The pair of probes are structured such that complementary portions at three or more sites are each hybridized in a specific manner without fail during one-to-one hybridization.

A target gene detecting method according to the present invention, in a first aspect, comprises the steps of providing a pair of probes, one of which has a gene in one portion thereof complementary to a target gene, hybridizing a plurality of said pairs of probes with the target gene by the gene amplifying method described above to form a double-stranded polymer, and amplifying the probes to detect the target gene.

An antigen/antibody detecting method according to the present invention, in a first aspect, comprises the steps of providing a pair of probes, one of which has a gene in one portion thereof complementary to a target gene bound to antigen/antibody, hybridizing a plurality of said pairs of probes with the target gene by the gene amplifying method described above to form a double-stranded polymer, and detecting antigen/antibody.

The target gene detecting method according to the present invention, in a second aspect, comprises the steps of providing a pair of probes and another probe complementary to a gene in a portion of one of said pair of probes and to a target gene, previously hybridizing said other probe to the target gene, hybridizing said pairs of probes with the target gene by the gene amplifying method described above to form a double-stranded polymer, and amplifying the probes to detect the target gene.

The antigen/antibody detecting method according to the present invention, in a second aspect, comprises the steps of providing a pair of probes and another probe complementary to a gene in a portion of one of said pair of probes and to a target gene bound to antigen/antibody, previously hybridizing said other probe to the target gene, and hybridizing said pairs of probes with the target gene by the gene amplifying method described above to form a double-stranded polymer, and detecting the antigen/antibody.

In the target gene detecting method, an intercalating dye such as ethidium bromide, Oligreen, SYBR Green or the like may be bound to the probes amplified by the gene amplifying method to detect an amplified polymer through fluorescence.

In the antigen/antibody detecting method according to the present invention, an intercalating dye such as ethidium bromide, Oligreen, SYBR Green or the like may be bound to the probes amplified by the gene amplifying method to detect the target gene bound to antigen/antibody or the like through fluorescence.

In the target gene detecting method according to the present invention, as a marker material for detection, a donor fluorescent dye and an acceptor fluorescent dye utilizing fluorescent resonance energy transfer (FRET) such as radioisotope such as $^{125}$I, $^{32}$P or the like, light emitting and coloring materials such as digoxigenin, acridine ester or the like, alkali phosphatase for utilizing a light emitting material such as dioxyethane or the like, and fluorescent materials such as 4-methyl umbelliferil phosphate or the like, and biotin for utilizing fluorescent, light emitting, coloring materials or the like bound to avidin, may be previously added to the probes to be amplified by the gene amplifying method to detect the target gene.

In the antigen/antibody detecting method according to the present invention, as a marker material for detection, a donor fluorescent dye and an acceptor fluorescent dye utilizing fluorescent resonance energy transfer (FRET) such as radioisotope such as $^{125}$I, $^{32}$P or the like, light emitting and coloring materials such as digoxigenin, acridine ester or the like, alkali phosphatase for utilizing a light emitting material such as dioxyethane or the like, and fluorescent materials such as 4-methyl umbelliferil phosphate or the like, and biotin for utilizing fluorescent, light emitting and coloring materials or the like bound to avidin, may be previously added to a pair of probes to be amplified by the gene amplifying method to detect the antigen/antibody.

Each of said probes according to the present invention is composed of three or more portions complementary to such portions of the other probe.

The pair of probes may be two DNA probes, a DNA probe and an RNA probe, two RNA probes, two PNA probes, a PNA probe and a DNA probe, or a PNA probe and an RNA probe.

A double-stranded polymer according to the present invention is formed by using a plurality of the pair of probes, and hybridizing them such that they cross in alternation.

The DNA probe is composed of single-stranded fragments mainly consisting of phosphoric acid, saccharum and bases (adenine, thymine, guanine and cytosine), while the RNA probe is composed of single-stranded fragments mainly consisting of bases which are adenine, uracil, guanine and cytosine. PNA has a structure in which the skeleton of "phosphoric acid and saccharum" in DNA is replaced by an "N-(2-aminoethyl) glycine derivative" and has the same components of bases as DNA and RNA.

The length of the probes for use in the methods mentioned above ranges from 10 bases to 1,000 bases, and most preferably from 10 bases to 100 bases.

The pair of probes are not particularly limited in the type of bases in the mutually complementary portions. In addition, the lengths of the complementary portions existing in one probe may be equal or different.

The number of probes hybridized to form a double-stranded polymer for use in the methods mentioned above is in a range of $10^2$ to $10^{15}$.

BRIEF DESCRIPTION OF THE DRAWINGS

FIG. 1 is a schematic diagram showing an example of a pair of DNA probes, Probe No. 1 (SEQ ID NO:13) and Probe No. 2 (SEQ ID NO:14);

FIG. 7 is a schematic diagram showing an example of a pair of DNA probes in which portions cleaved by a restriction enzyme are inserted; wherein Probes No. 3 and 4 are SEQ ID NO:3 and SEQ ID NO:4, respectively;

FIG. 9 is a schematic diagram showing an example of a pair of DNA probes each composed of complementary portions having different lengths from each other; wherein Probes No. 5 and 6 are SEQ ID NO:15 and SEQ ID NO:16, respectively;

FIG. 10 is a schematic diagram illustrating the formation of a polymer resulting from alternate hybridization of the pair of DNA probes, shown in FIG. 9.

FIG. 14 is a photograph showing the results of Example 1;

DETAILED DESCRIPTION OF THE PREFERRED EMBODIMENTS

Several embodiments of the present invention will hereinafter be described with reference to the accompanying drawings. It goes without saying, however, that these embodiments are merely illustrative, and a variety of modifications may be made without departing from the spirit and scope of the present invention.

FIG. 1 is a schematic diagram showing an example of a pair of DNA probes. Referring specifically to FIG. 1, a DNA probe No. 1 has an X-region, a Y-region and a Z-region, while a DNA probe No. 2 has an X'-region, a Y'-region and a Z'-region.

Figure 2:
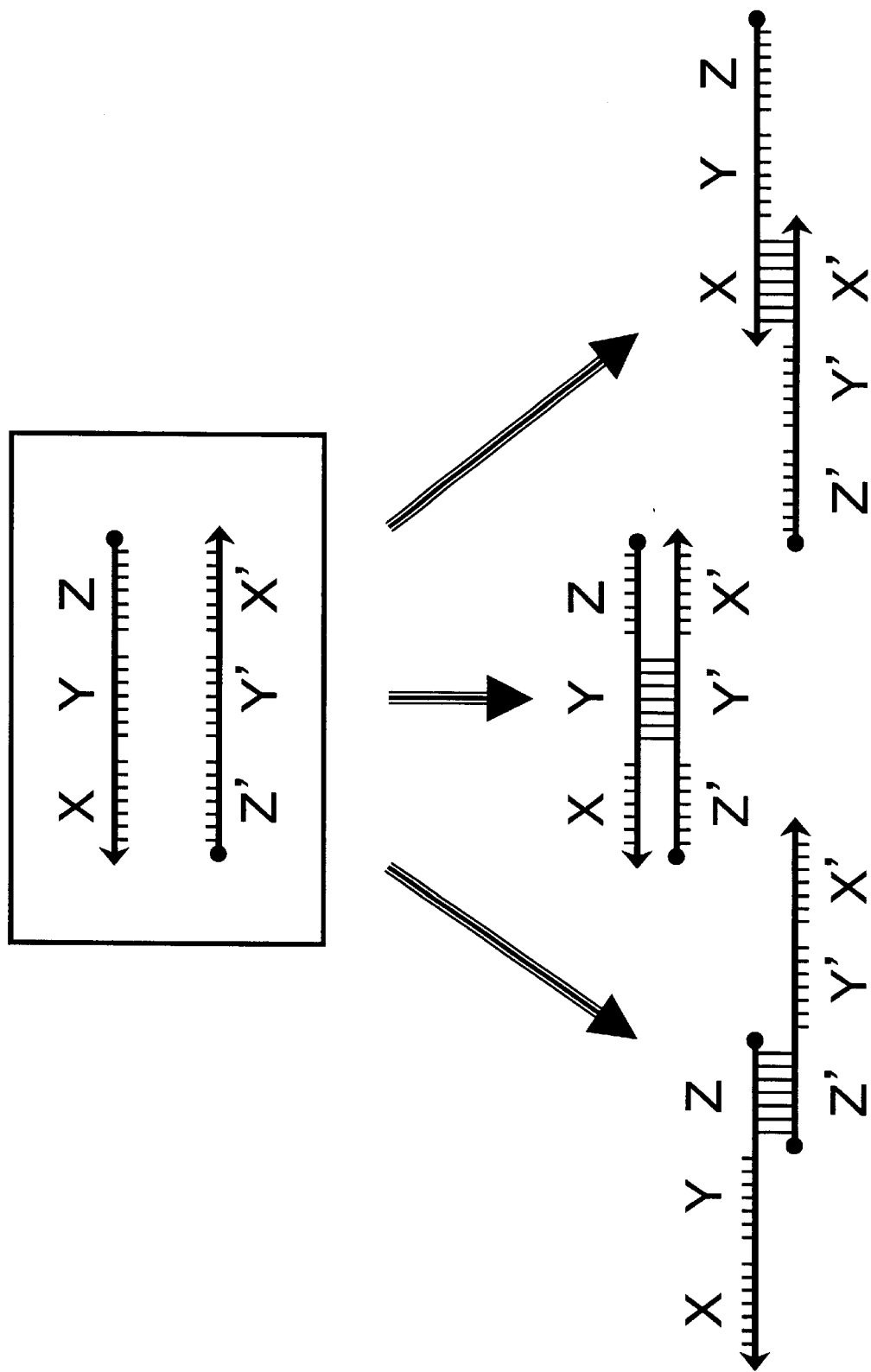
FIG. 2 is a schematic diagram of an example showing how a pair of DNA probes are bound.

The DNA probe No. 1 and the DNA probe No. 2 are structured such that when they are hybridized, the X-region is bound only with the X'-region; the Y-region is bound only with the Y'-region; and the Z-region is bound only with the Z'-region (see FIG. 2).

Stated another way, with a pair of DNA probes each composed of three or more portions complementary to such portions of the other DNA probe, according to the present invention, when they are hybridized such that they cross in alternation, the X-region is bound only with the X'-region; the Y-region is bound only with the Y'-region; and the Z-region is bound only with the Z'-region, as shown in FIG. 2, so that the pair of probes are hybridized in alternation in three binding patterns.

Thus, by the use of the probes structured as mentioned above, the two probes are bound in alternation. Specifically, the DNA probe No. 1 and the DNA probe No. 2 are three-dimensionally bound in alternation to produce a polymer, as illustrated in FIG. 3.

Figure 3:
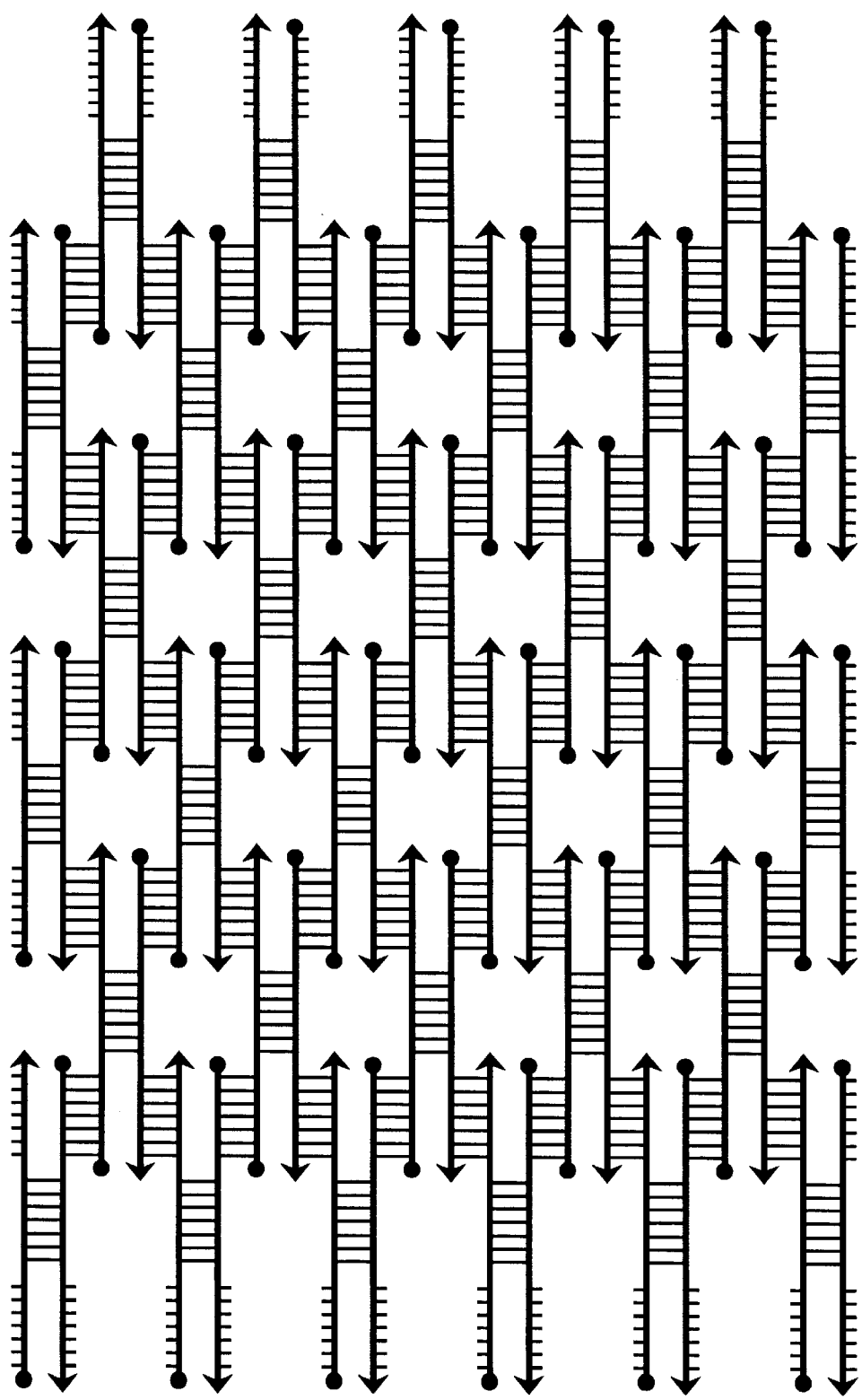
FIG. 3 is a schematic diagram showing the formation of a polymer resulting from hybridization of a pair of DNA probes in alternation.

Consequently, a plurality of pairs of probes, which have been hybridized in alternation in the three binding patterns shown in FIG. 2, can form a double-stranded polymer, one example of which is schematically illustrated in FIG. 3.

Figure 4:
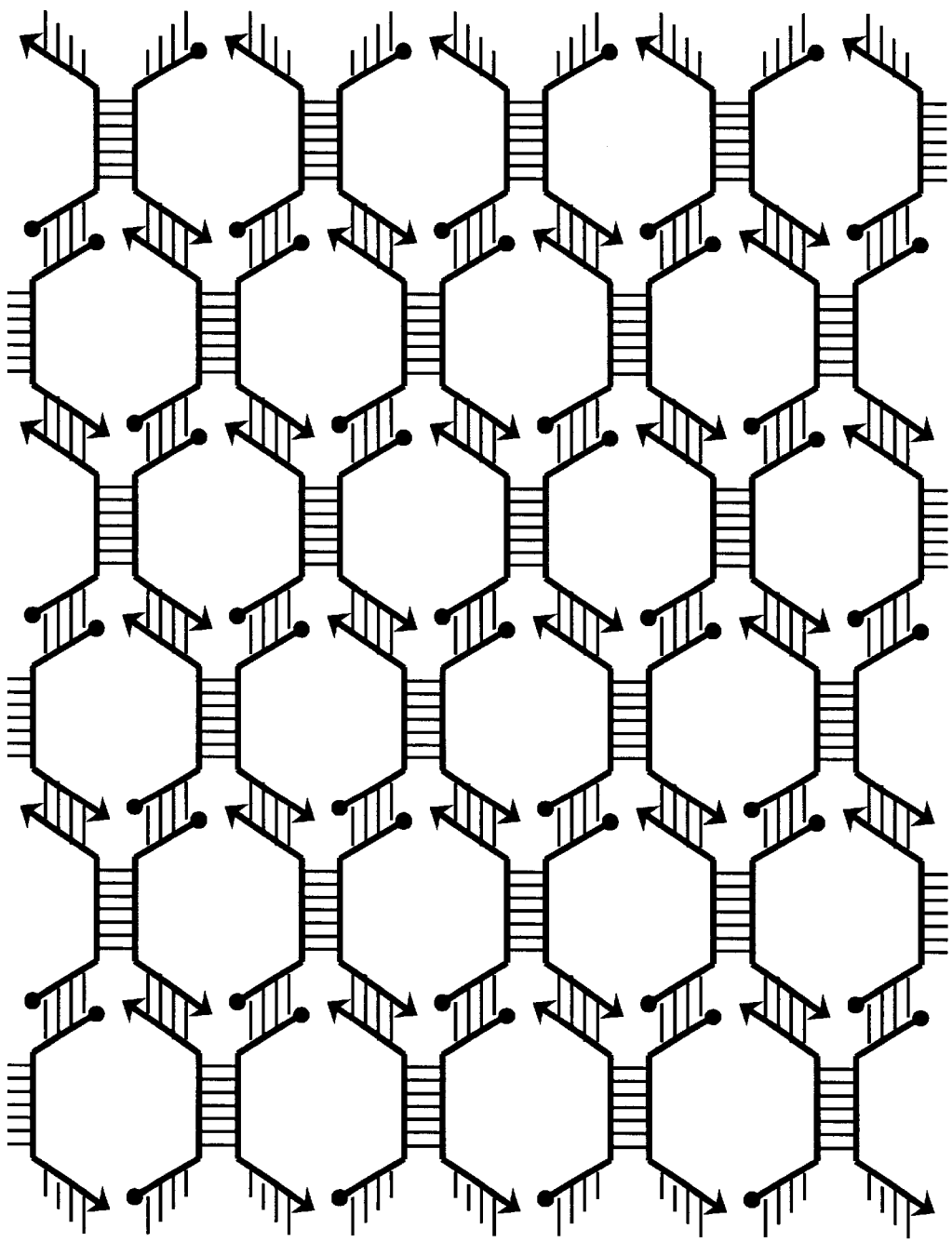
FIG. 4 is a schematic diagram illustrating an example of a three-dimensional conceptual structure of the polymer shown in FIG. 3.
Figure 5:
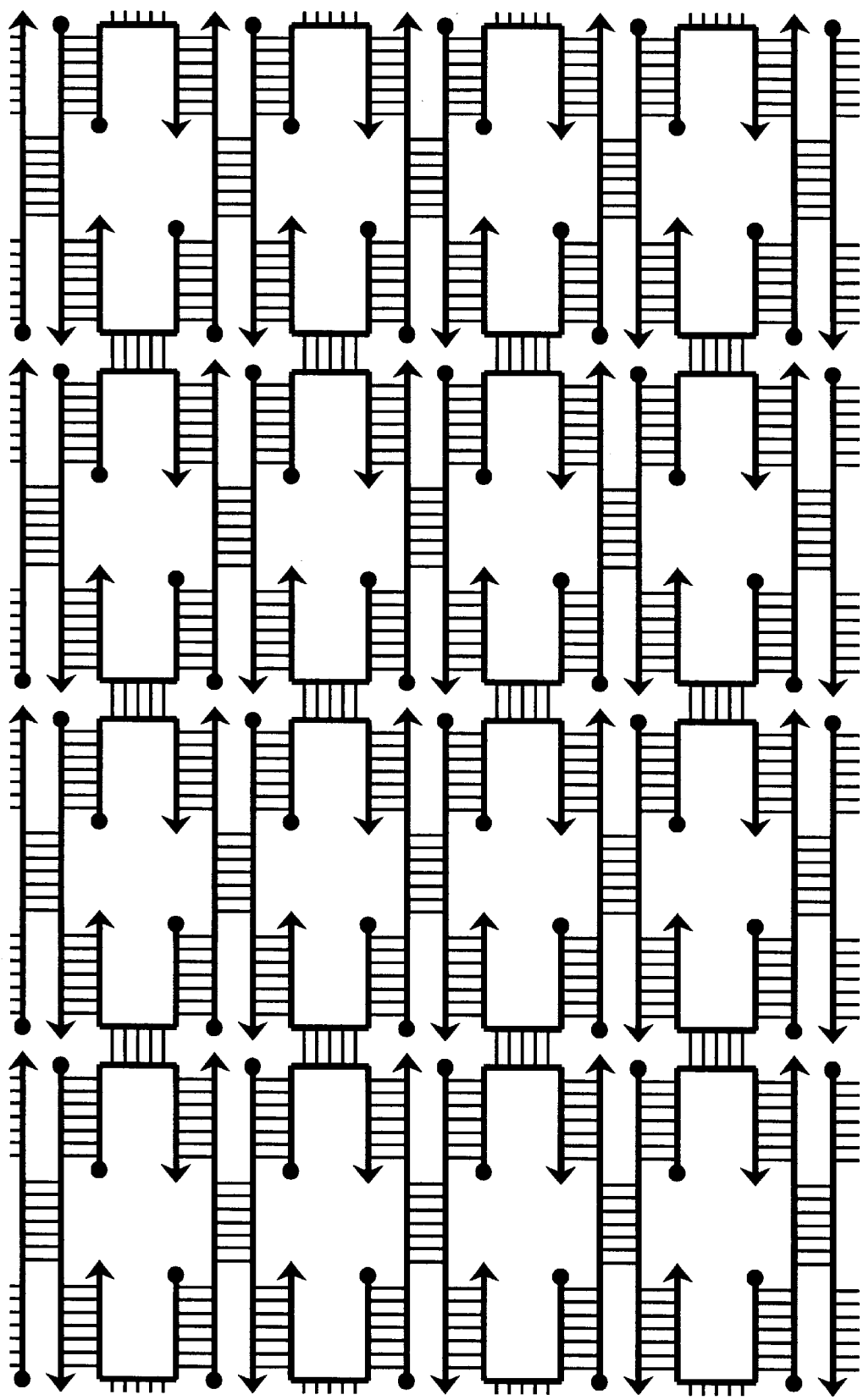
FIG. 5 is a schematic diagram illustrating DNA probes which are hybridized in binding patterns different from those of FIG. 3.
Figure 6:
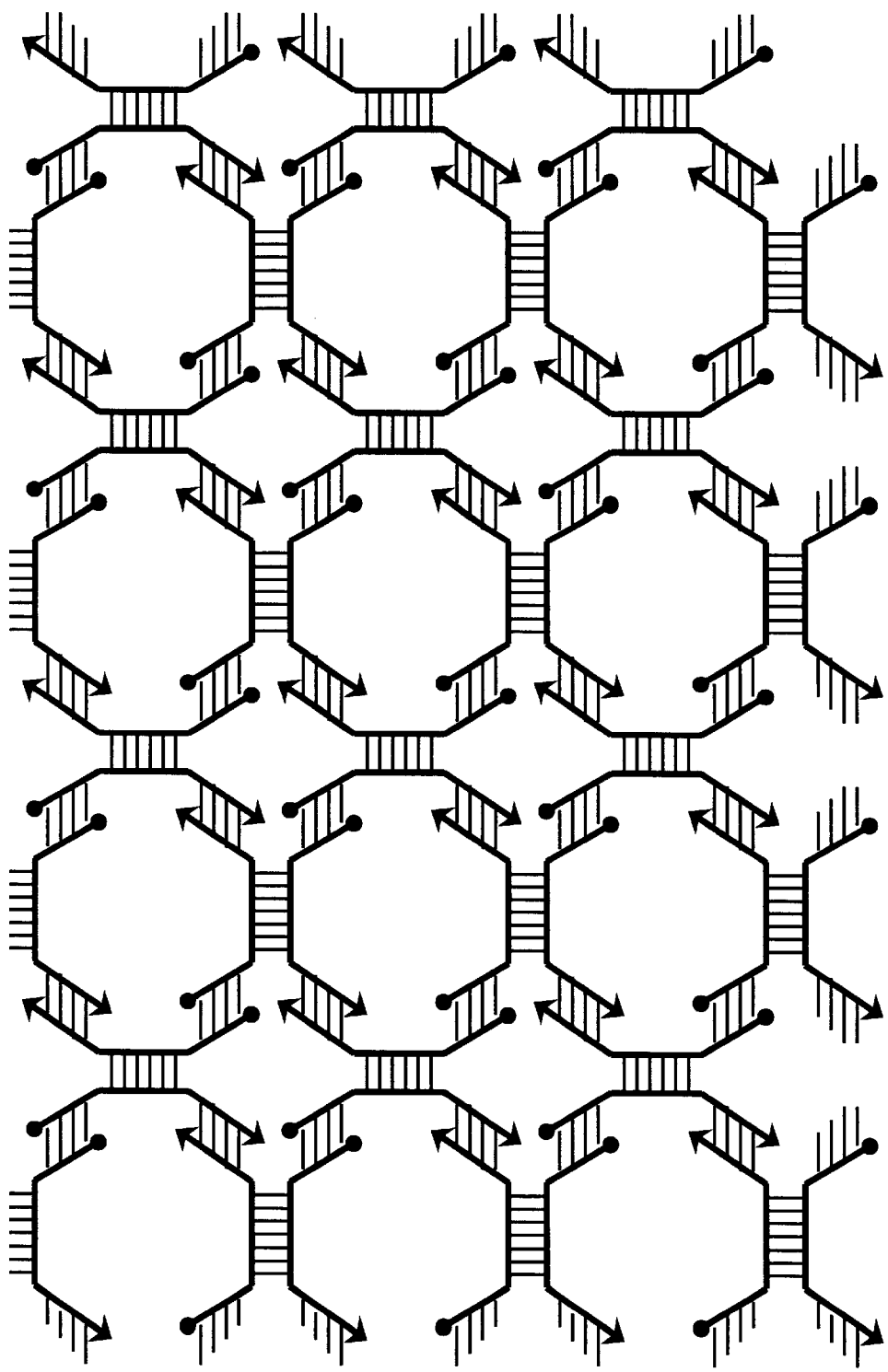
FIG. 6 illustrates an example of a three-dimensional conceptual structure of the schematic diagram of FIG. 5.

FIG. 4 illustrates an example of a three-dimensional conceptual structure of the double-stranded polymer of FIG. 3. FIG. 5 is a schematic diagram illustrating a plurality of pairs of the DNA probes which have been hybridized in different binding patterns. FIG. 6 illustrates an example of a three-dimensional conceptual structure of the schematic diagram of FIG. 5.

The same principle of hybridization for the two DNA probes illustrated in FIG. 3 applies to hybridization of a DNA probe and an RNA probe, two RNA probes, two PNA probes, a PNA probe and a DNA probe, or a PNA probe and an RNA probe.

Illustrating the structure of the present invention using a more specific example, the hybridization of two DNA probes may be performed such that when a probe No. 3 and a probe No. 4 are hybridized, cleaved sites are formed by a restriction enzyme (underlined portions are cleaved by an enzyme called "Hae III"), as shown in FIG. 7.

Figure 8:
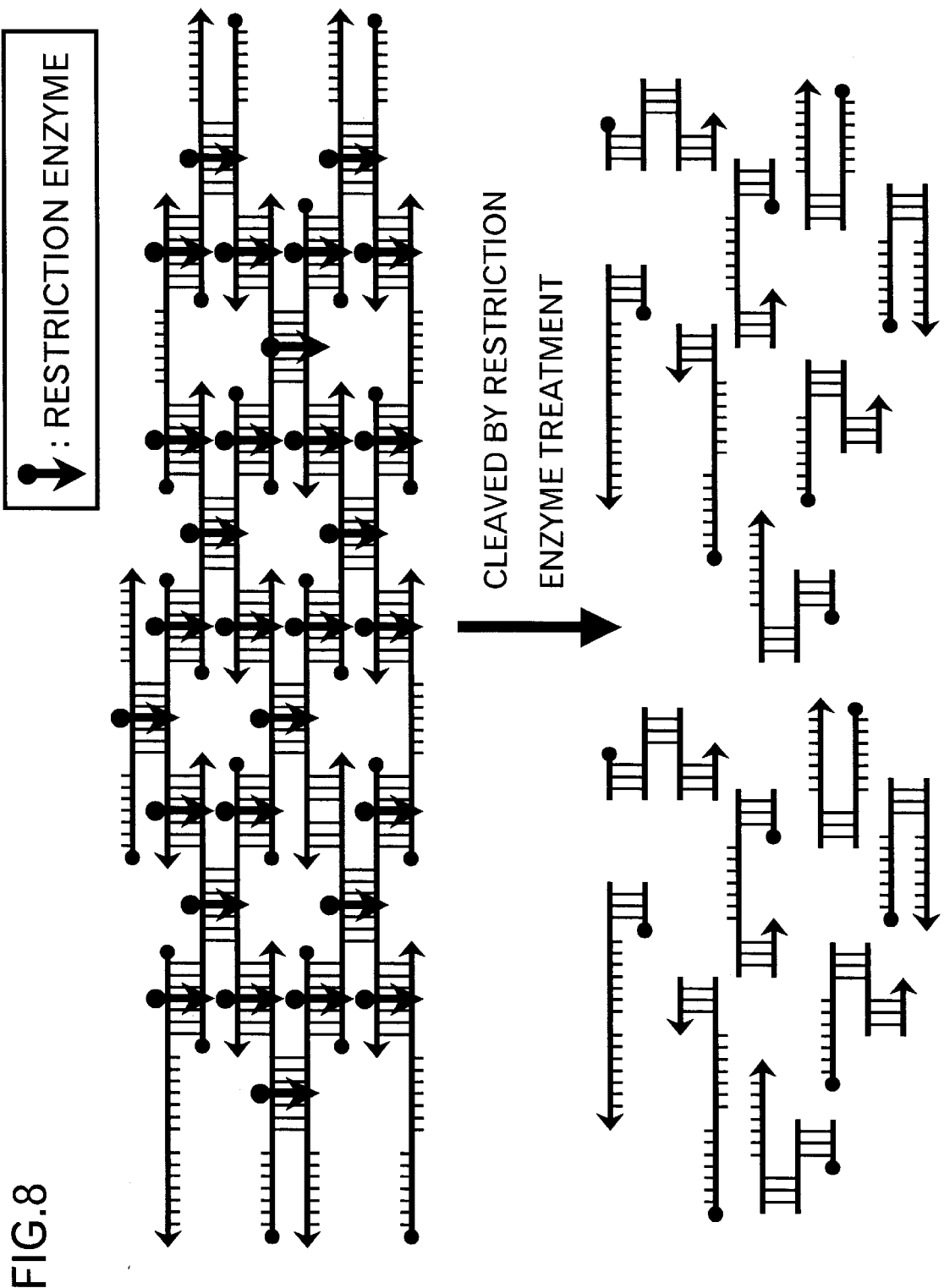
FIG. 8 is a schematic diagram illustrating an example in which probes are three-dimensionally bound in alternation to form a polymer which is subsequently cleaved using a restriction enzyme.

In other words, after the probes have three-dimensionally bound in alternation to form a polymer, a restriction enzyme can be used to prevent the polymer from cross-contamination in a subsequent different experimental operation (see FIG. 8).

Illustrating the structure of the present invention using a more specific example, the hybridization of two DNA probes does not require that the lengths of complementary portions in one probe be uniform, as shown in FIG. 9. Specifically, when a probe No. 5 and a probe No. 6 are hybridized, an X-region and an X'-region are hybridized with 24 bases; a Y-region and a Y'-region hybridize with 22 bases; and a Z-region and a Z'-region hybridize with 20 bases (see FIG. 10).

Figure 11:
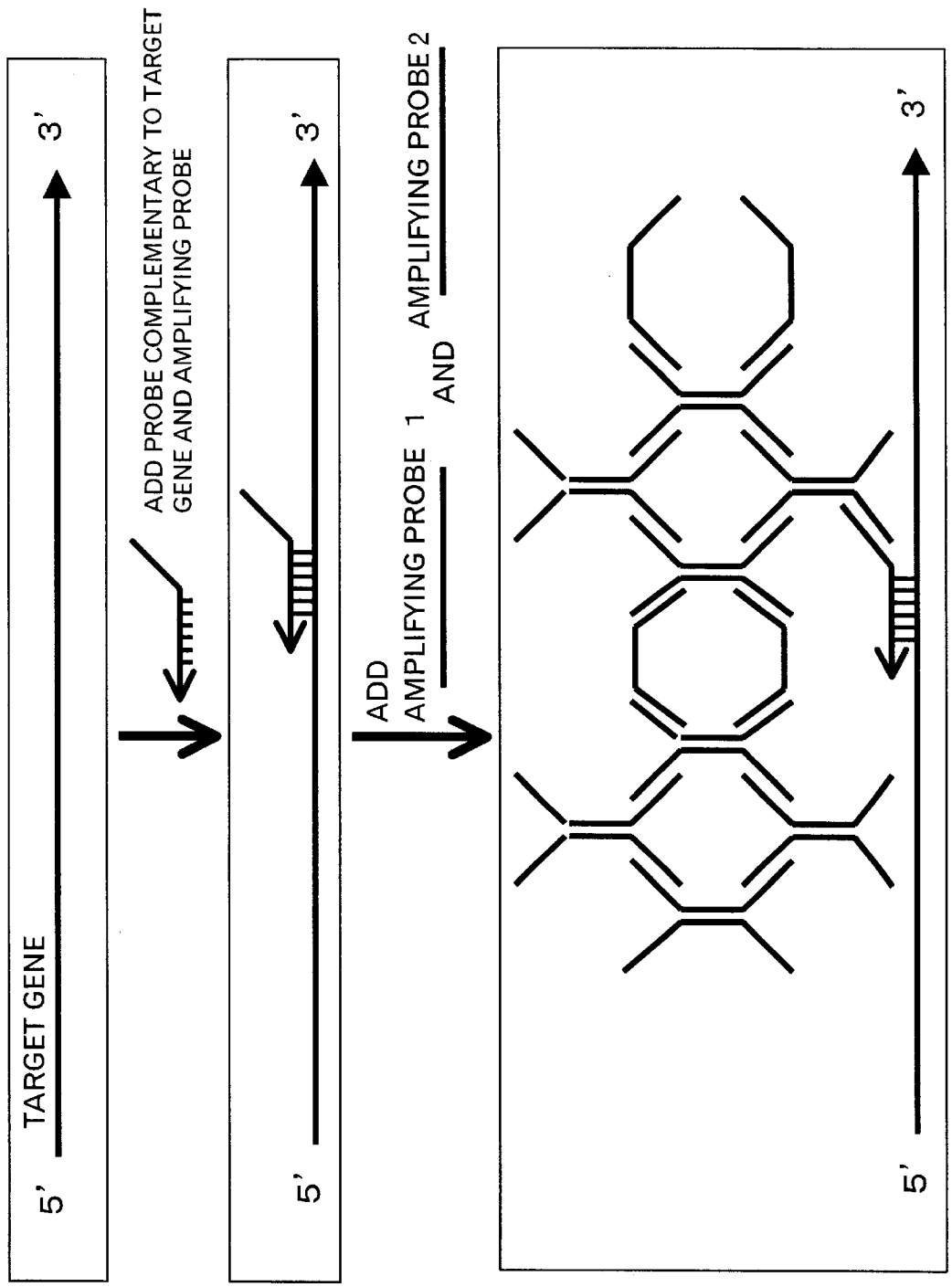
FIG. 11 is a schematic diagram showing a method of directly detecting a target gene using a pair of DNA probes according to the present invention, wherein a probe having complementary regions to a target gene and the pair of DNA probes according to the present invention (amplifying genes in the figure) is hybridized to the target gene, and then the pair of DNA probes according to the present invention (amplifying gene 1 and amplifying gene 2 in the figure) are added to form a double-stranded polymer while hybridized to the target gene, so that the target gene can be readily detected.

Next, the target gene detecting method according to the present invention will be described using more specific examples. In a first aspect as illustrated in FIG. 11, out of a pair of probes, one probe is structured such that a portion of gene in the probe is complementary to a target gene. After the one probe is hybridized with the target gene, a plurality of the pairs of probes are hybridized by the gene amplification method according to the present invention to form a double-stranded polymer which is detected by amplifying the probes.

Figure 12:
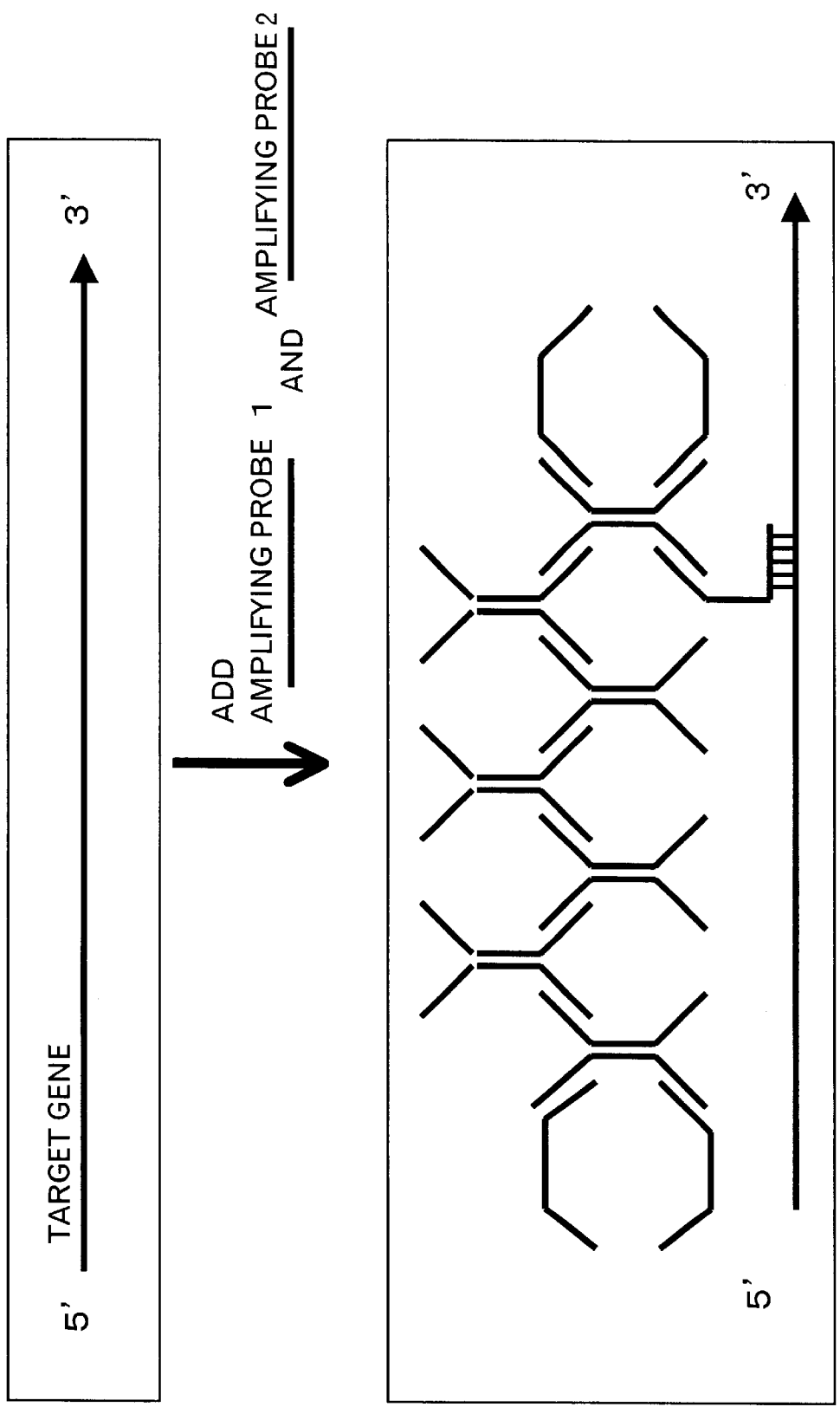
FIG. 12 is a schematic diagram showing a method of detecting a target gene which uses a pair of DNA probes, one of which is a DNA probe (amplifying gene 1 in the figure) structured such that a gene in a portion thereof is complementary to a target gene, and the other of which is a DNA probe (amplifying gene 2 in the figure) making a pair with the one DNA probe, hybridizes a plurality of the pairs of probes with the target probe to form a double-stranded polymer, and detects the target gene.

In a second aspect as illustrated in FIG. 12, other than a pair of probes, a probe complementary to a gene in a portion of one of the probes and a target probe is used, and previously hybridized with the target gene. Then, a plurality of the pairs of probes are hybridized by the gene amplifying method mentioned above to form a double-stranded polymer which is detected by amplifying the probes.

Figure 13:
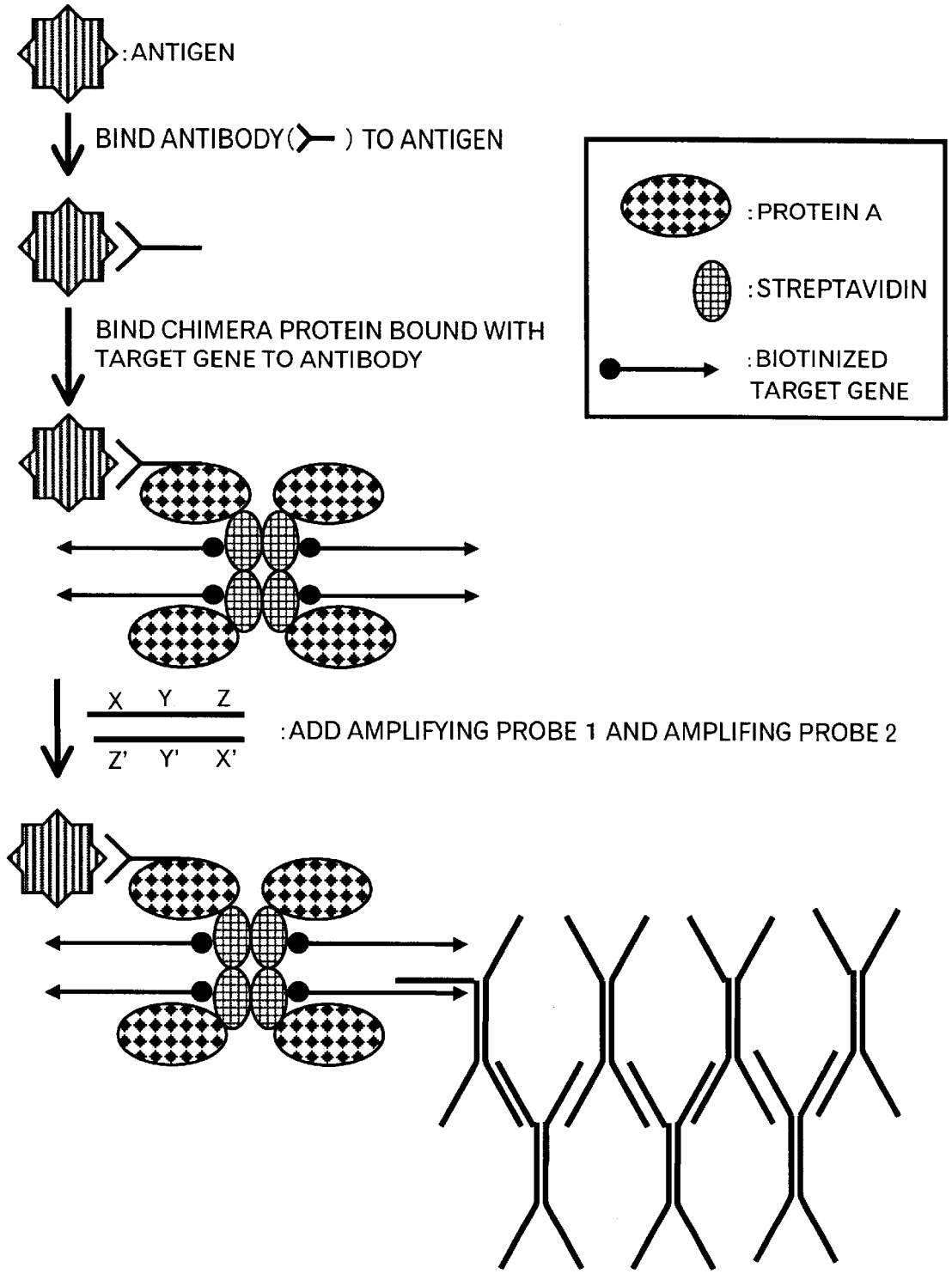
FIG. 13 is a flow diagram illustrating a first aspect of an antigen/antibody detecting method according to the present invention.

Next, a first aspect of an antigen/antibody detecting method according to the present invention will be described using a more specific example with reference to FIG. 13. As illustrated, out of a pair of probes, one probe is structured such that a gene in a portion thereof is complementary to a target gene bound to antigen/antibody. Then, a plurality of the pairs of probes are hybridized by the gene amplifying method according to the present invention to form a double-stranded polymer to detect the antigen and the antibody.

In the following, the present invention will be described in conjunction with several examples. It goes without saying, however, that the present invention is not limited to these examples.

1. DNA Probes used in Example 1 and Example 2

(1) Gene Amplifying Probe 1 (SEQ ID NO:1)

5-TgA CTT ACT TAA CCg gAA ACA T.AAg CAg gAT CCT CTA AgC CTg A.CgA AgT ATT TAA Cgg Tgg TAT g-3

(2) Gene Amplifying Probe 2 (SEQ ID NO:2)

3-gCT TCA TAA ATT gCC ACC ATA C.TTC gTC CTA ggA gAT TCg gAc T.ACT gAA TgA ATT ggC CTT TgT A-5

(3) Gene Amplifying Probe 3 (SEQ ID NO:3)

5'-TgC CgA CCg gCg AgC g.TAg CAT ggC CCT CTA g.CTT ATC ggC CTC gAg A -3'

(4) Gene Amplifying Probe 4 (SEQ ID NO:4)

3'-gAA TAg CCg gAg CTC T.ATC gTA CCg ggA gAT C.ACg gCT ggC CgC TCg C -5'

2. Synthetic HCV-RNA and a Variety of DNA Probes Used in Example 3 and Example 4

(1) HCV-RNA which Synthesizes a 5'-noncoding Region of Hepatitis C Virus (hereinafter abbreviated as "synthesized HCV-RNA).

(2) HCV-RNA capture Probe A (SEQ ID NO:5)

5'(phosphoric acid)-TAg AgC gTg CAg ATA gTC gAT.CCT CAC Agg ggA gTg ATT CAT ggT-3'

This is a combination of a meaningless base sequence and a base sequence complementary to HCV-RNA.

(3) HCV-RNA Capture Probe B (SEQ ID NO:6)

5'(biotin label)-TAg AgC gTg CAg ATA gTC gAT.CCT CAC Agg ggA gTg ATT CAT ggT-3'

This is a combination of a meaningless base sequence and a base sequence complementary to HCV-RNA.

(4) Probe C (SEQ ID NO:7)

3'-TAC TTA gTg Agg ggA CAC TCC.gAA TAA gTC ATA gCT CAT-5'

This is a combination of a base sequence complementary to HCV-RNA and a base sequence complementary to the amplifying probe 5.

(5) Probe D (SEQ ID NO:8)

3'-gCC CAg gAA AgA ACC TAg TTg. gAA TAA gTC ATA gCT CAT-5'

This is a combination of a base sequence complementary to HCV-RNA and a base sequence complementary to the amplifying probe 5.

(6) Probe E (SEQ ID NO:9)

3'-CAT CAC AAC CCA gCg CTT TCC.gAA TAA gTC ATA gCT CAT- 5'

This is a combination of a base sequence complementary to HCV-RNA and a base sequence complementary to the amplifying probe 5.

(7) Gene Amplifying Probe 5 (SEQ ID NO:10)

5'-CTT ATT CAg TAT CgA gTA.TAg CAg gAT CCC TCT AAg.TgC Cgg ACC AgC gAg Cgg-3'

This is a base sequence complementary to the capture probes B, C, D.

(8) Gene Amplifying Probe 6 (SEQ ID NO:11)

3'-ACg gCC Tgg TCg CTC gCC.ATC gTC CTA ggg AgA TTC.gAA TAA gTC ATA gCT CAT-5'

(9) Gene Amplifying Probe 7 (SEQ ID NO:12)

3'(biotinized)-ACg gCC Tgg TCg CTC gCC.ATC gTC CTA ggg AgA TTC.gAA TAA gTC ATA gCT CAT-5'

EXAMPLE 1

1. Object

The effect of gene amplification with respect to the temperature of hybridization was proved using gene amplifying probes which are a pair of DNA probes according to the present invention.

2. Materials

1) The probe 1 for gene amplification and the probe 2 for gene amplification were used for gene amplification.

2) 20×SSC (333 mM—NaCl, 333 mM—$C_6H_5O_7Na_3 \cdot 2H_2O$, pH 7.0) was used as a buffering solution.

3. Method

5 μL of the gene amplifying probe 1 and the gene amplifying probe 2 each prepared to be $10^{13}$ copies/μL were added in a sterilized microtube of 0.2 mL, respectively. 40μL of 20×SSC was further added, and the microtube was covered with a lid. Then, the microtube was boiled at 94° C. for 30 seconds, and warmed at 50° C., 52° C., 54° C., 56° C., 60° C., 62° C., 64° C., 66° C., 68° C. and 70° C. for 30 minutes, respectively.

After the warming, electrophoresis was performed using 0.5% agarose gel to confirm the effect of the gene amplification through ethidium bromide coloring.

4. Results

FIG. 14 is a photograph showing the results of Example 1 with electrophoresis at 100 volts for 30 minutes using 0.5% agarose gel.

The agarose gel is a gel which can divide DNA molecules according to the size, and 0.5% agarose gel is generally used to separate DNA molecules of 30,000–40,000 base pairs.

The photograph of FIG. 14 shows a polymer which has grown so much with increasing temperatures that it can no longer migrate with 0.5% agarose gel as a result of an exactly alternate double-stranded polymer formed by the pair of DNA probes depending on the temperature of hybridization.

EXAMPLE 2

1. Object

It was proved that a polymer amplified by probes for gene amplification, which are a pair of DNA probes according to the present invention, can be cleaved by a restriction enzyme.

2. Materials

1) The gene amplifying probe 3 and the gene amplifying probe 4 were used for gene amplification.

2) Hae III (made by Takara Shuzo (brewer) Co., Ltd.) was used as a restriction enzyme.

3) M-Buffer (made by Takara Shuzo (brewer) Co., Ltd.) was used as a buffering solution for restriction enzyme.

4) 20×SSC (333 mM—NaCl, 333 mM—$C_6H_5O_7Na_3 \cdot 2H_2O$, pH 7.0) was used as a buffering solution.

3. Method

5μL of the gene amplifying probe 3 and the gene amplifying probe 4 each prepared to be $10^{13}$ copies/μL were added in a sterilized microtube of 0.2 mL, respectively. 5 μL of 20×SSC and 35 μL of sterilized distilled water were further added to produce a reaction solution A, and the microtube was covered with a lid. Similarly to the reaction solution A, 2.5 μL of the gene amplifying probe 3 and the gene amplifying probe 4 each prepared to be $10^{13}$ copies/μL were added in a sterilized microtube of 0.2 mL, respectively. 5 μL of 20×SSC and 40 μL of sterilized distilled water were further added to produce a reaction solution B, and the microtube was covered with a lid. The reaction solutions A, B were boiled at 94° C. for 30 seconds, and warmed at 62° C. for 30 minutes, respectively.

After the warming, 5 μL of M-Buffer and 5 μL of Hae III were added to each of the reaction solutions A, B for reaction at 37° C. for 24 hours, and electrophoresis was performed using 2% agarose gel to confirm an amplified polymer cleaved by the restriction enzyme through ethidium bromide coloring.

4. Results

Figure 15:
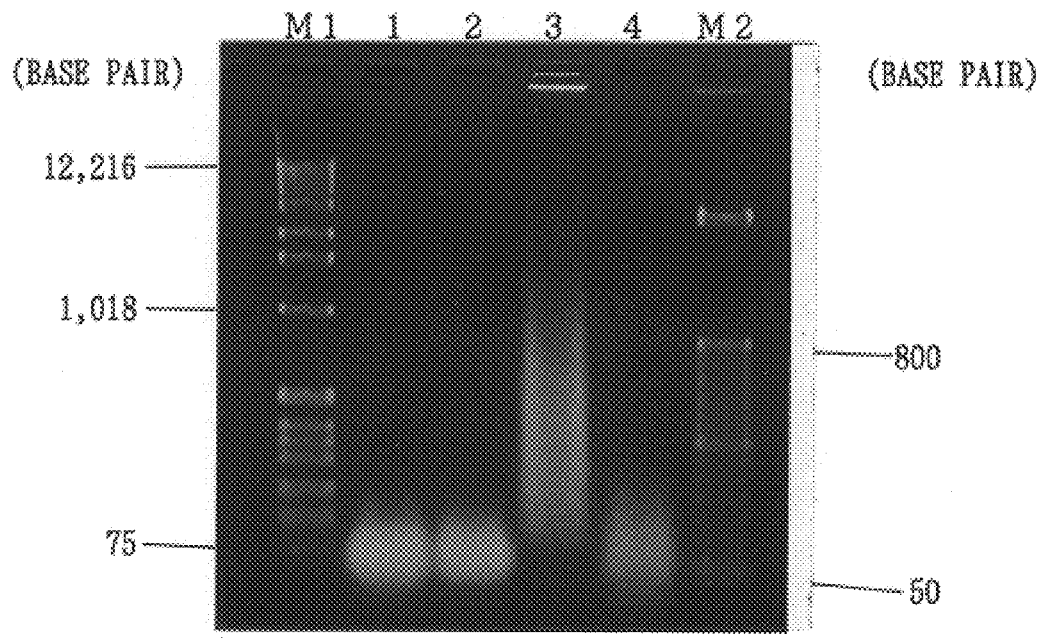
FIG. 15 is a photograph showing the results of Example 2.

FIG. 15 is a photograph showing the results of Example 2 with electrophoresis at 100 volts for 30 minutes using 2% agarose gel. The photograph shows that a pair of DNA probes forming a exactly alternate double-stranded polymer is was cleaved to minimum units by the restriction enzyme.

EXAMPLE 3

1. Materials

1) The gene amplifying probe 5 and the gene amplifying probe 6 were used for gene amplification.

2) Magnetic beads bound with streptavidin (product name: Streptavidin MagneSphere made by Promega) was used for a solid phase for B/F separation.

3) 20×SSC and 0.5×SSC (40-times diluent of 20×SSC) were used as buffering solutions.

2. Method

10 μL each of synthetic HCV-RNA prepared to be $10^1$ copy/10 μL, $10^2$ copy/10 μL, $10^3$ copy/10 μL, $10^4$ copy/10 μL, $10^5$ copy/10 μL, $10^6$ copy/10 μL, $10^7$ copy/10 μL, $10^8$ copy/10 μL, $10^9$ copy/10 μL, and $10^{10}$ copy/10 μL were each added in a sterilized microtube of 0.2 mL. Next, 1 μL each of the HCV-RNA capture probe B, probe C, probe D and probe E prepared to be $10^{13}$ copies/μL, 10 μL of the gene amplifying probe 5 prepared to be $10^{13}$ copies/μL, and 25 μL of 20×SSC were added. The respective microtubes were covered with a lid, the ingredyents were mixed by a mixer, and warmed at 62° C. for 60 minutes.

Once the temperature lowered to a room temperature, 5 μL of the gene amplifying probe 6 prepared to be $10^{13}$ copies/μL was added to each of the microtubes. Then, each of the microtubes was covered with a lid, and the ingredyents were mixed by a mixer and warmed at 62° C. for 60 minutes.

Once the temperature lowered to a room temperature, 10 μL of Streptavidin MagneSphere (hereinafter called the "magnetic beads") was added to each of the microtubes for reaction at 37° C. for 30 minutes. After the reaction, the magnetic beads were trapped using a magnet, and supernatant was removed. Then, 50 μL of 0.5×SSC and 10 μL of ethidium bromide (made by Wako Junyaku Co., Ltd.) prepared to be 100 μg/mL were added for reaction at a room temperature for 20 minutes.

After the reaction, the magnetic beads were trapped using a magnet, and supernatant was removed. Then, 50 μL of 0.5×SSC was added. Immediately, the magnetic beads were trapped using a magnet, and supernatant was removed. Then, 50 μL of 0.5×SSC was added, and all ingredients were transferred to a flat-bottom 96 well plate. Ultraviolet rays were irradiated from the bottom of the 96 well plate, and an amplified gene, which ended up to emit fluorescence by intercalation of ethidium bromide, was photographed.

3. Results

Figure 16:
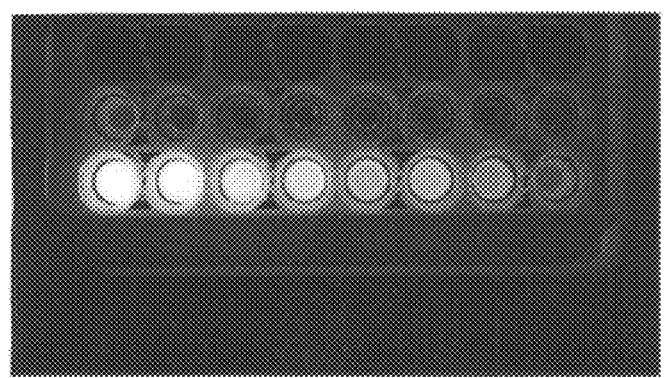
FIG. 16 is a photograph showing the results of Example 3.

FIG. 16 is a photograph showing the fluorescence by the ethidium bromide produced by irradiating ultraviolet rays from the bottom of the 96 well plate. As can be seen in FIG. 16, the strongest fluorescence was found at $10^{10}$ copies/10 μL, and the fluorescence became gradually weaker in accordance with the amount of synthetic HCV-RNA.

EXAMPLE 4

1. Materials

1) The gene amplifying probe 5 and the gene amplifying probe 7 were used for gene amplification.

2) A 96 well plate (product name: NucleoLink™ made by Nunc) was used for a solid phase for B/F separation.

3) "HPR-Streptavidin" made by ZYMED Laboratories, Inc. was used as Peroxidase Conjugated Streptavidin.

4) A coloring kit T for peroxidase made by Sumitomo Bakelite Co., Ltd. was used as a coloring reagent.

5) 2N—$H_2SO_4$ was used for an enzyme reaction stop solution.

6) 20×SSC and 0.5×SSC were used as buffering solutions.

2. Method

10 μL each of synthetic HCV-RNA prepared to be 0 copy/10 μL, $10^3$ copies/10 μL, $10^4$ copies/10 μL, $10^5$ copies/10 μL, $10^6$ copies/10 μL, and $10^7$ copies/10 μL were added to each of wells in a 96 well plate (NucleoLink™ made by Nunc) previously bound with the HCV-RNA capture probe A (special blocking was not applied). Then, 10 μL each of the probe C, probe D, probe E prepared to be $10^{11}$ copies/μL, 10 μL of the gene amplifying probe 5 prepared to be $10^{11}$ copies/μL, and 60 μL of 20×SSC were added.

After mixing the ingredyents by a pipette, they were heated at 94° C. for 30 seconds, and warmed at 62° C. for 60 minutes.

Once the temperature lowered to a room temperature, 10 μL of the gene amplifying probe 5 prepared to be $10^{11}$ copies/μL, and 20 μL of the gene amplifying probe 7 were added to each of the microtubes. They were mixed by a pipette, and then heated at 94° C. for 30 seconds, and warmed at 62° C. for 60 minutes.

After the temperature lowered to a room temperature, 0.5×SSC including 0.1%-Tween20 was used to wash four times. 100 μL of "HRP-Streptavidin" was added in each well, and warmed at 37° C. for 20 minutes. After removing the solution in each well by means of suction, 0.5×SSC including 0.1%-Tween20 was used to wash four times.

100 μL of the coloring kit T for peroxidase was added to each well for reaction in a dark room (at a room temperature) for 10 minutes. After the reaction, 100 μL of the enzyme reaction stop solution was added, and the light absortion was measured at wavelength of 450 nm.

3. Results

The results of Example 4 are shown in Table 1 below. Coloring was confirmed in accordance with the amount of added synthesized HCV-RNA in a range of $10^3$ to $10^7$ copies from the fact that coloring was observed in Peroxidase Conjugated Streptavidin labelled at one of a pair of DNA probes which were hybridized in alternation to form a double-stranded polymer.

TABLE 1

| Number of Copies | Absorbance |
| --- | --- |
| 0 | 1.497 |
| $10^3$ | 1.843 |
| $10^4$ | 1.897 |
| $10^5$ | 1.955 |
| $10^6$ | 2.064 |
| $10^7$ | 2.343 |

As described above, the gene amplifying method according to the present invention efficiently amplify a gene without using a DNA polymerase or branched DNA.

Also, the antigen/antibody detecting method according to the present invention can efficiently detect antigen/antibody by making use of the gene amplifying method.

Obviously various minor changes and modifications of the present invention are possible in the light of the above teaching. It is therefore to be understood that within the scope of the appended claims the invention may be practiced otherwise than as specifically described.

What is claimed is:

1. A method of forming a nucleic acid polymer, the method comprising
   (a) providing a plurality of pairs of nucleic acid probes, each probe being 10 to 1000 bases in length, a first probe of said pair of probes comprising 3 or more nucleic acid regions, said first probe comprising at least a nucleic acid region X, a nucleic acid region Y and a nucleic acid region Z and having the following structure

, and a second probe of said pair of probes comprising 3 or more nucleic acid regions, said second probe comprising at least a nucleic acid region Z', a nucleic acid region Y' and a nucleic acid region X' and having the following structure

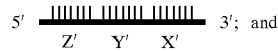; and (b) by binding said plurality of pairs of probes to each other to form a polymer, wherein said nucleic acid region X is hybridizable with said nucleic acid region X', said nucleic acid region Y is hybridizable with said nucleic acid region Y' and said nucleic acid region Z is hybridizable with said nucleic acid region Z' such that said plurality of pairs of probes form the following structures

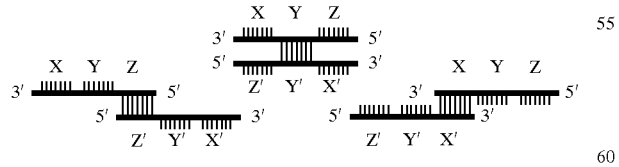

which structures are bound with each other in alternation to form said polymer.

2. The method of claim 1, wherein said pair of probes comprises two DNA probes, a DNA probe and an RNA probe, two RNA probes, two PNA probes, a PNA probe and a DNA probe, or a PNA probe and an RNA probe.

3. The method of claim 1, wherein said nucleic acid region X is completely complementary with said nucleic acid region X', said nucleic acid region Y is completely complementary with said nucleic acid region Y' and said nucleic acid region Z is completely complementary with said nucleic acid region Z'.

4. The method of claim 1, wherein said polymer is a network or web.

5. A method of detecting a target gene, the method comprising
   (a) providing a plurality of pairs of nucleic acid probes, each probe being 10 to 1000 based in length, a first probe of said pair of probes comprising 3 or more nucleic acid regions, said first probe comprising at least a nucleic acid region X, a nucleic acid region Y and a nucleic acid region Z and having the following structure

, and a second probe of said pair of probes comprising 3 or more nucleic acid regions, said second probe comprising at least a nucleic acid region Z', a nucleic acid region Y' and a nucleic acid region X' and having the following structure

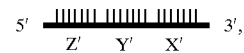, wherein a sequence of one probe of said pair of probes is complementary to a sequence of said target gene;

(b) binding said target gene and said plurality of pairs of probes to each other such that said plurality of pairs of probes form a polymer, wherein said nucleic acid region X is hybridizable with said nucleic acid region X', said nucleic acid region Y is hybridizable with said nucleic acid region Y' and said nucleic acid region Z is hybridizable with said nucleic acid region Z' such that said plurality of pairs of probes form the following structures

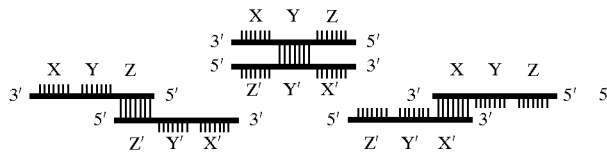

which structures are bound with each other in alternation to form said polymer; and (c) detecting said polymer, thereby detecting said target gene.

6. The method of claim 5, wherein said pair of probes comprises two DNA probes, a DNA probe and an RNA probe, two RNA probes, two PNA probes, a PNA probe and a DNA probe, or a PNA probe and an RNA probe.

7. The method of claim 5, wherein said nucleic acid region X is completely complementary with said nucleic acid region X', said nucleic acid region Y is completely complementary with said nucleic acid region Y' and said nucleic acid region Z is completely complementary with said nucleic acid region Z'.

8. The method of claim 5, wherein said detecting step (c) comprises incorporating a fluorescent material into said polymer, and thereafter detecting said fluorescent material.

9. The method of claim 5, wherein at least one probe of said plurality of pairs of probes includes a marker material, and said detecting step (c) comprises detecting said marker material.

10. The method of claim 5, wherein said polymer is a network or web.

11. A method of detecting an antigen/antibody complex having a target gene bound thereto, the method comprising (a) providing a plurality of pairs of nucleic acid probes, each of said probes being 10 to 1000 bases in length, a first probe of said pair of probes comprising 3 or more nucleic acid regions, said first probe comprising at least a nucleic acid region X, a nucleic acid region Y and a nucleic acid region Z and having the following structure

a second probe of said pair of probes comprising 3 or more nucleic acid regions, said second probe comprising at least a nucleic acid region Z', a nucleic acid region Y' and a nucleic acid region X' and having the following structure

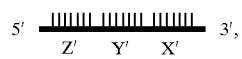

wherein a sequence of one probe of said pair of probes is complementary to a sequence of said target gene bound to said antigen/antibody complex;

(b) binding said target gene and said plurality of pairs of probes to each other such that said plurality of pairs of probes form a polymer, wherein said nucleic acid region X is hybridizable with said nucleic acid region X', said nucleic acid region Y is hybridizable with said nucleic acid region Y' and said nucleic acid region Z is hybridizable with said nucleic acid region Z' such that said plurality of pairs of probes form the following structures

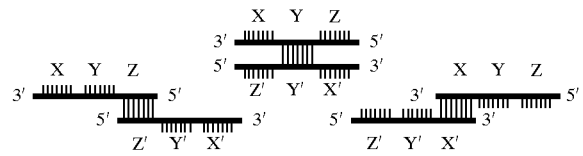

which structures are bound with each other in alternation to form said polymer; and (c) detecting said polymer, thereby detecting said antigen/antibody complex.

12. The method of claim 11, wherein said pair of probes comprises two DNA probes, a DNA probe and an RNA probe, two RNA probes, two PNA probes, a PNA probe and a DNA probe, or a PNA probe and an RNA probe.

13. The method of claim 11, wherein said nucleic acid region X is completely complementary with said nucleic acid region X', said nucleic acid region Y is completely complementary with said nucleic acid region Y' and said nucleic acid region Z is completely complementary with said nucleic acid region Z'.

14. The method of claim 11, wherein said detecting step (c) comprises incorporating a fluorescent material into said polymer, and thereafter detecting said fluorescent material.

15. The method of claim 11, wherein at least one probe of said plurality of pairs of probes includes a marker material, and said detecting step (c) comprises detecting said marker material.

16. The method of claim 11, wherein said polymer is a network or web.

17. A method of detecting a target gene, the method comprising (a) providing (1) a plurality of pairs of nucleic acid probes, each probe being 10 to 1000 bases in length, a first probe of said pair of probes comprising 3 or more nucleic acid regions, said first probe comprising at least a nucleic acid region X, a nucleic acid region Y and a nucleic acid region Z and having the following structure

a second probe of said pair of probes comprising 3 or more nucleic acid regions, said second probe comprising at least a nucleic acid region Z', a nucleic acid region Y' and a nucleic acid region X' and having the following structure

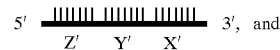

(2) a further probe which contains a first sequence which is complementary to a sequence of said target gene and which contains a second sequence which is complementary to a sequence of one probe of said pair of probes;

(b) binding said target gene, said further probe and said plurality of pairs of probes to each other such that said plurality of pairs of probes form a polymer, wherein said nucleic acid region X is hybridizable with said nucleic acid region X', said nucleic acid region Y is hybridizable with said nucleic acid region Y' and said nucleic acid Z is hybridizable with said nucleic acid region Z' such that said plurality of pairs of probes form the following structures

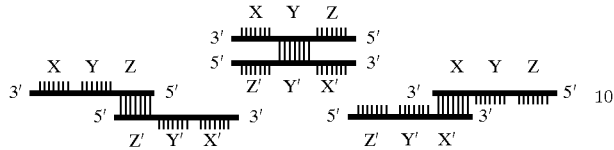

which structures are bound with each other in alternation to form said polymer; and (c) detecting said polymer, thereby detecting said target gene.

18. The method of claim 17, wherein said pair of probes comprises two DNA probes, a DNA probe and an RNA probe, two RNA probes, two PNA probes, a PNA probe and a DNA probe, or a PNA probe and an RNA probe.

19. The method of claim 17, wherein said nucleic acid region X is completely complementary with said nucleic acid region X', said nucleic acid region Y is completely complementary with said nucleic acid region Y' and said nucleic acid region Z is completely complementary with said nucleic acid region Z'.

20. The method of claim 17, wherein said detecting step (c) comprises incorporating a fluorescent material into said polymer, and thereafter detecting said fluorescent material.

21. The method of claim 17, wherein at least one probe of said plurality of pairs of probes includes a marker material, and said detecting step (c) comprises detecting said marker material.

22. The method of claim 17, wherein said polymer is a network or web.

23. A method of detecting an antigen/antibody complex having a target gene bound thereto, the method comprising (a) providing (1) a plurality of pairs of nucleic acid probes, each probe being 10 to 1000 bases in length, a first probe of said pair of probes comprising 3 or more nucleic acid regions, said first probe comprising at least a nucleic acid region X, a nucleic acid region Y and a nucleic acid region Z and having the following structure

a second probe of said pair of probes comprising 3 or more nucleic acid regions, said second probe comprising at least a nucleic acid region Z', a nucleic acid region Y' and a nucleic acid region X' and having the following structure

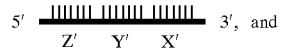

(2) a further probe which contains a first sequence which is complementary to a sequence of said target gene bound to said antigen/antibody complex and which contains a second sequence which is complementary to a sequence of one probe of said pair of probes;

(b) binding said target gene, said further probe and said plurality of pairs of probes to each other such that said plurality of pairs of probes form a polymer, wherein said nucleic acid region X is hybridizable with said nucleic acid region X', said nucleic acid region Y is hybridizable with said nucleic acid region Y' and said nucleic acid region Z is hybridizable with said nucleic acid region Z' such that said plurality of pairs of probes form the following structures

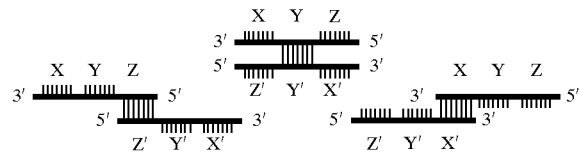

which structures are bound with each other in alternation to form said polymer; and (c) detecting said polymer, thereby detecting said antigen/antibody complex.

24. The method of claim 23, wherein said pair of probes comprises two DNA probes, a DNA probe and an RNA probe, two RNA probes, two PNA probes, a PNA probe and a DNA probe, or a PNA probe and an RNA probe.

25. The method of claim 23, wherein said nucleic acid region X is completely complementary with said nucleic acid region X', said nucleic acid region Y is completely complementary with said nucleic acid region Y' and said nucleic acid region Z is completely complementary with said nucleic acid region Z'.

26. The method of claim 23, wherein said detecting step (c) comprises incorporating a fluorescent material into said polymer, and thereafter detecting said fluorescent material.

27. The method of claim 23, wherein at least one probe of said plurality of pairs of probes includes a marker material, and said detecting step (c) comprising detecting said marker material.

28. The method of claim 23, wherein said polymer is a network or web.

29. A pair of nucleic acid probes, each probe being 10 to 1000 bases in length, a first probe of said pair of probes comprising 3 or more nucleic acid regions, said first probe comprising at least a nucleic acid region X, a nucleic acid region Y and a nucleic acid region Z and having the following structure

a second probe of said pair of probes comprising 3 or more nucleic acid regions, said second probe comprising at least a nucleic acid region Z', a nucleic acid region Y' and a nucleic acid region X' and having the following structure

wherein said nucleic acid region X is hybridizable with said nucleic acid region X', said nucleic acid region Y is hybridizable with said nucleic acid region Y' and said nucleic acid region Z is hybridizable with said nucleic acid region Z' such that said pair of probes forms one of the following structures

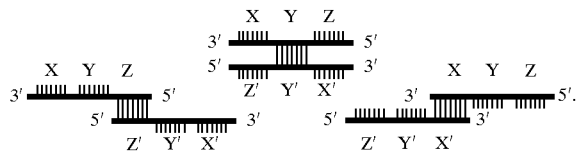 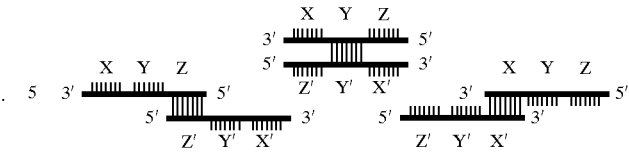

30. The pair of probes of claim 29, wherein said pair of probes comprises two DNA probes, a DNA probe and an RNA probe, two RNA probes, two PNA probes, a PNA probe and a DNA probe, or a PNA probe and an RNA probe.

31. A polymer, comprised of a plurality of pairs of probes according to claim 29, wherein said plurality of pairs of probes form the following structures which structures are bound with each other in alternation to form said polymer.

32. The polymer of claim 29, wherein said pair of probes comprises two DNA probes, a DNA probe and an RNA probe, two RNA probes, two PNA probes, a PNA probe and a DNA probe, or a PNA probe and an RNA probe.

33. The polymer of claim 29, which is a network or web.

* * * * *

UNITED STATES PATENT AND TRADEMARK OFFICE
CERTIFICATE OF CORRECTION

PATENT NO. : 6,261,846 B1
DATED : July 17, 2001
INVENTOR(S) : Mitsugu Usui

It is certified that error appears in the above-identified patent and that said Letters Patent is hereby corrected as shown below:

Column 15, claim 1,
Line 46, delete "by".

Signed and Sealed this

Fifth Day of March, 2002

*Attest:*

*Attesting Officer*

JAMES E. ROGAN
*Director of the United States Patent and Trademark Office*